(12) United States Patent
Chin et al.

(10) Patent No.: US 7,749,149 B2
(45) Date of Patent: *Jul. 6, 2010

(54) MINIATURE X-RAY UNIT

(75) Inventors: Yem Chin, Burlington, MA (US);
Charles H. Pugsley, Jr., Pelham, NH (US); David W. Hoffman, Westborough, MA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 1480 days.

This patent is subject to a terminal disclaimer.

(21) Appl. No.: 11/059,924

(22) Filed: Feb. 17, 2005

(65) Prior Publication Data

US 2005/0185765 A1 Aug. 25, 2005

Related U.S. Application Data

(63) Continuation of application No. 10/360,502, filed on Feb. 6, 2003, now Pat. No. 6,910,999, which is a continuation of application No. 09/710,304, filed on Nov. 10, 2000, now Pat. No. 6,540,655.

(51) Int. Cl.
*A61N 5/00* (2006.01)
(52) U.S. Cl. ...................................................... 600/3
(58) Field of Classification Search ................ 600/1–8; 604/19–21; 378/65
See application file for complete search history.

(56) References Cited

U.S. PATENT DOCUMENTS

| | | | | |
|---|---|---|---|---|
| 4,459,990 A * | 7/1984 | Barnea | ...................... | 600/433 |
| 5,578,008 A * | 11/1996 | Hara | ...................... | 604/96.01 |
| 5,816,999 A * | 10/1998 | Bischoff et al. | ................ | 600/3 |
| 6,148,061 A * | 11/2000 | Shefer et al. | ................ | 378/121 |
| 6,540,655 B1 * | 4/2003 | Chin et al. | ..................... | 600/3 |
| 6,910,999 B2 * | 6/2005 | Chin et al. | ..................... | 600/3 |

* cited by examiner

*Primary Examiner*—John P Lacyk
(74) *Attorney, Agent, or Firm*—Vista IP Law Group LLP (57) ABSTRACT

A miniaturized x-ray apparatus for delivering x-rays to a selected site within a body cavity includes a catheter having at least one lumen and an x-ray transparent window at a distal end thereof; an x-ray source in the lumen adjacent said x-ray transparent window; a movable x-ray shield positioned to direct x-rays from the source through the x-ray transparent window to the selected site.

28 Claims, 6 Drawing Sheets

MINIATURE X-RAY UNIT

This application is a continuation application of U.S. Ser. No. 10/360,502 filed Feb. 6, 2003, now U.S. Pat. No. 6,910,999 which is a continuation of U.S. Ser. No. 09/710,304 filed Nov. 10, 2000, now U.S. Pat. No. 6,540,655 B1, each of which is incorporated herein by reference in its entirety.

FIELD OF THE INVENTION

The invention relates to a miniaturized x-ray source situated in a catheter that generates x-rays while minimizing risk from exposure to the x-rays.

BACKGROUND OF THE INVENTION

Traditionally, x-rays have been used in the medical industry to view bone, tissue and teeth. X-rays have also been used to treat cancerous and precancerous conditions by exposing a patient to x-rays using an external x-ray source. Treatment of cancer with x-rays may cause well documented side effects, many of which are due to the broad exposure of the patient to the therapeutic x-rays.

To improve medical treatment and diagnosis of patients, minimally invasive endoscopic techniques have been developed and are used to treat a variety of conditions. Endoluminal procedures are procedures performed with an endoscope, a tubular device into the lumen of which may be inserted a variety of rigid or flexible tools to treat or diagnose a patient's condition.

The desire for improved minimally invasive medical devices and techniques have led to the development of miniaturized x-ray devices that may be used in the treatment or prevention of a variety of medical conditions. International Publication No. WO 98/48899 discloses a miniature x-ray unit having an anode and cathode separated by a vacuum gap positioned inside a metal housing. The anode includes a base portion and a projecting portion. The x-ray unit is insulated and connected to a coaxial cable which, in turn, is connected to the power source. An x-ray window surrounds the projecting portion of the anode and the cathode so that the x-rays can exit the unit. The x-ray unit is sized for intra-vascular insertion, and may be used, inter alia, in vascular brachytherapy of coronary arteries, particularly after balloon angioplasty.

International Publication No. WO 97/07740 discloses an x-ray catheter having a catheter shaft with an x-ray unit attached to the distal end of the catheter shaft. The x-ray unit comprises an anode and a cathode coupled to an insulator to define a vacuum chamber. The x-ray unit is coupled to a voltage source via a coaxial cable. The x-ray unit can have a diameter of less than 4 mm and a length of less than about 15 mm, and can be used in conjunction with coronary angioplasty to prevent restenosis.

Miniaturized x-rays are not foolproof, however, and still present difficulties upon use. The x-ray unit generates heat, which can damage adjacent healthy tissue. Additionally, the x-rays are not localized and irradiate local tissue rather than only irradiating the desired tissue. It is difficult to maintain the positioning of these instruments at the desired location. Improved miniaturized x-ray units that overcome these difficulties are desirable.

Other techniques are used to treat tumors with radiation, including planting a seed of radioactive material at the tumor site, a procedure that is typically accomplished with endoluminal procedures. However, the patient becomes "hot", i.e., radioactive, and the procedure risks exposure of the medical personnel to radiation.

As noted above, many types of cancerous and precancerous conditions are treated by externally irradiating the tumor or site with x-rays. However, the x-rays are broadcast over a large area of healthy tissue in addition to the tumor because the radiation is administered from outside the body so that it penetrates the skin and any internal organs or tissue to reach the desired site. To avoid this, miniaturized x-ray systems which generate x-rays at the desired site are a desirable alternative to conventional apparatus.

Since many types of cancer occur in a body cavity or lumen, such as in the rectum, vagina, esophagus or pulmonary passages, it would be desirable to treat these cancers using miniaturized x-ray sources in combination with endoscopic techniques, which are minimally invasive to the patient, so that the cancer or other intraluminal tissue is directly treated with x-rays. This technique would minimize exposure of healthy tissues to the x-rays.

The present invention overcomes the difficulties associated with x-ray therapy and apparatus of the prior art by providing an endoscopic x-ray device that generates x-rays at the site of treatment and minimizes exposure of other tissues to irradiation.

SUMMARY OF THE INVENTION

A miniaturized x-ray apparatus for delivering x-rays to a selected site within a body cavity includes a catheter having at least one lumen and an x-ray transparent window at a distal end thereof; an x-ray source in the lumen adjacent said x-ray transparent window; a movable x-ray shield positioned to direct x-rays from the source through the x-ray transparent window to the selected site. The x-ray device ranges from 2 mm to about 15 mm.

The x-ray source is positioned inside an x-ray shielded catheter lumen, i.e., the catheter lumen is impenetrable by x-rays except in the area of the x-ray transparent window which is described in more detail below.

The x-ray source includes a cathode and an anode and an insulating material. The anode and cathode are separated by a vacuum gap. Insulating material may surround the base anode and cathode.

Preferably, a separate lumen of the catheter includes a camera through which medical personnel may observe the body lumen and procedure.

In a preferred embodiment, inflatable (anchoring or positioning) balloons are provided on the exterior of the endoscope to maintain the desired position of the instrument once inserted into the lumen. These balloons may be filled with a gas via catheter lumens connected to a gas or fluid source. Preferably, the balloons are filled with a fluid that absorbs x-rays so that the fluid will help prevent irradiation of undesired tissue. The gas and or fluid will also preferably help to absorb heat generated during the procedure to prevent burning of local tissue. A thermocouple may be positioned on the exterior of the endoscope to monitor the temperature at the treatment site.

In an alternative embodiment, the catheter includes an x-ray source and the anchoring balloons which are inflatable with gas or fluid as described above. This embodiment does not include a shield.

Another alternative embodiment provides a catheter having a miniaturized x-ray device and a stationary x-ray shield having an x-ray transparent window.

The invention is described in further detail hereinbelow.

DETAILED DESCRIPTION

Figures 1, 2, 3:
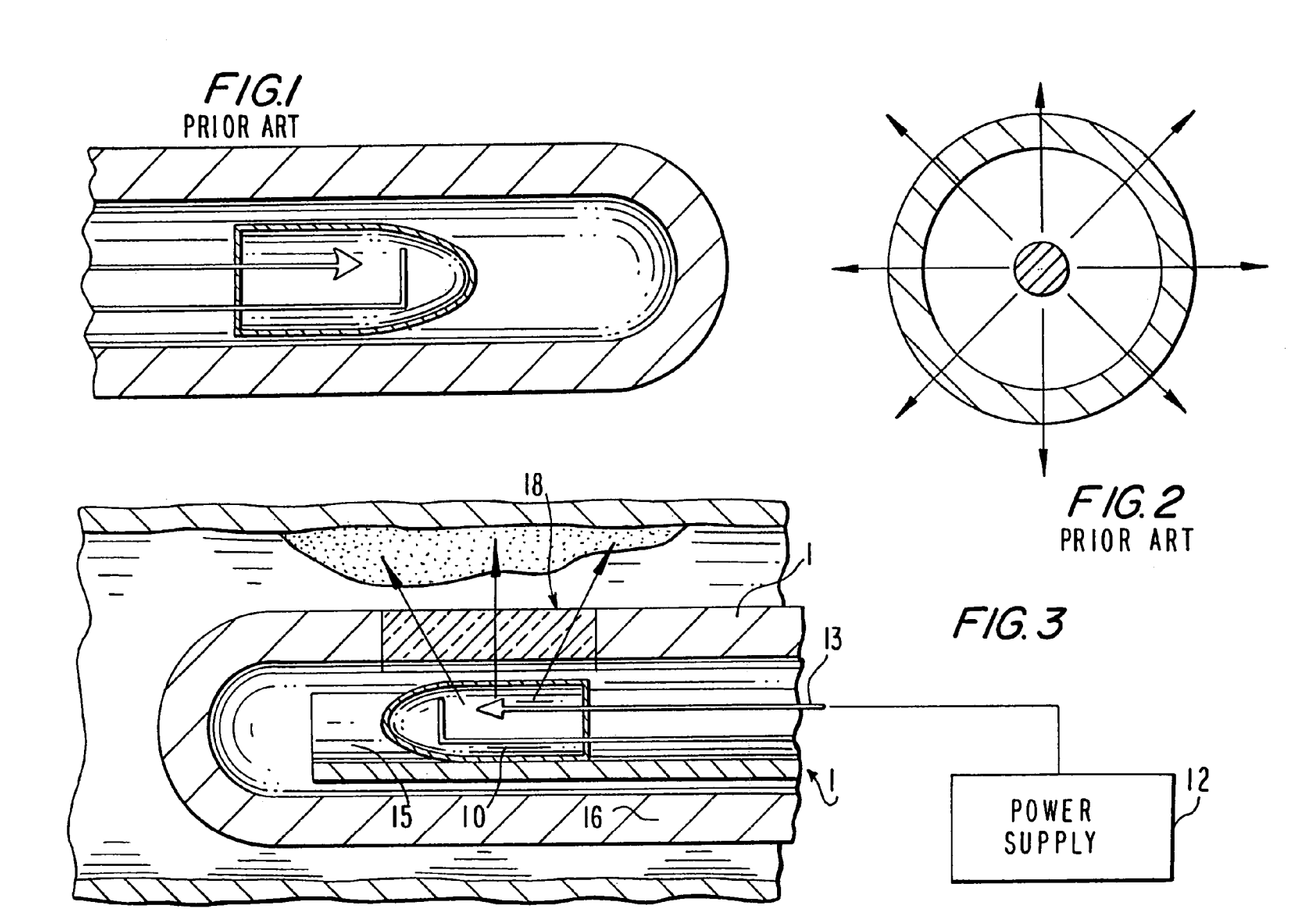
FIG. 1 is a is a miniaturized x-ray device according to the prior art.
FIG. 2 is the x-ray emission pattern from the device in FIG. 1.
FIG. 3 is a longitudinal cross section of a miniaturized x-ray device of the present invention.

FIG. 3 is a longitudinal cross section of a preferred x-ray apparatus according to the invention, inserted through the working channel of a endoscope (not shown) in a bodily lumen at a tumor site. The device 1 includes an x-ray source 10 which is connected to power supply 12 by electrically conductive cable 13, e.g. a coaxial cable. X-ray source 10 includes a vacuum tube which maintains vacuum conditions therein and houses the electrodes of the x-ray source. Power supply 12 delivers sufficient energy to x-ray source 10 to generate therapeutically effective x-rays. Typically, voltages of from 10 to 60 kilovolts (kV) are needed to generate x-rays from x-ray source 10. X-ray source 10 is located inside the lumen of x-ray tube 16 which is made of a material substantially or completely impenetrable to x-rays like lead or steel, except where x-ray transparent window 18 is positioned so that x-rays may exit the device and reach the desired site. Window 18 may circumferentially extend about the entire circumference of the x-ray tube 16, or may only be extend partially about the circumference of the x-ray tube.

Suitable materials for the window include beryllium, glass, ceramic, plastic, mica. Additional coatings of metal or insulating material may be layered or coated on the window material as needed.

Figure 4A:
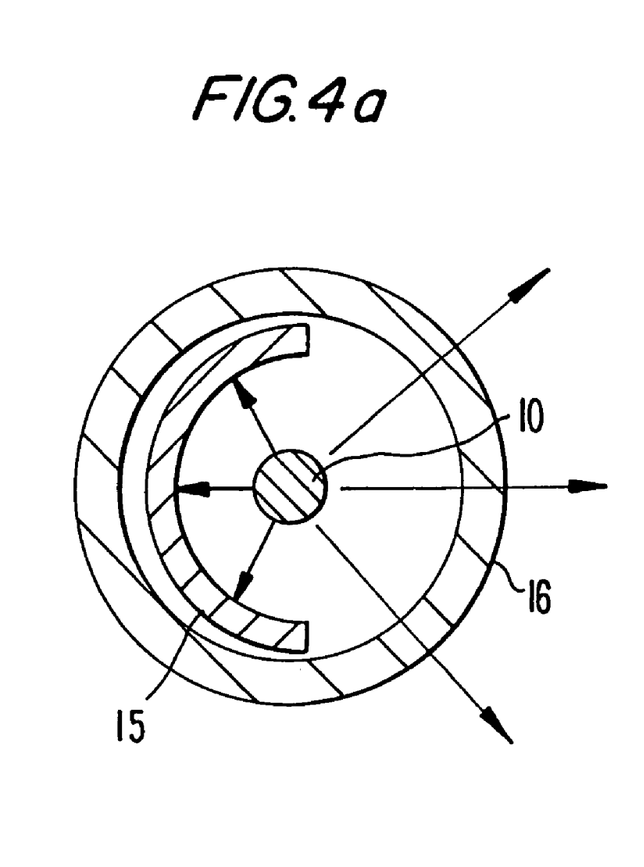
FIGS. 4a and 4b are axial cross-sections of the device of FIG. 3 showing the rotational motion of the x-ray shield about a central axis.
Figure 4B:
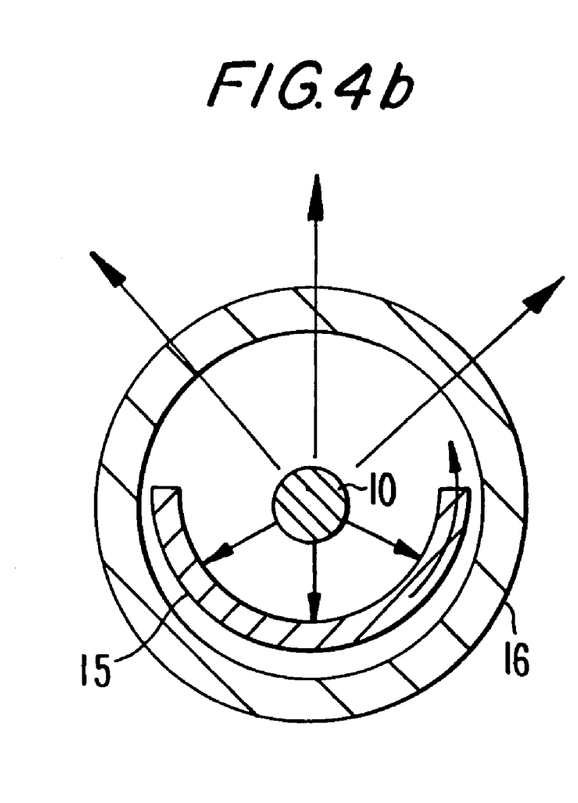

X-ray shield 15 is made of a material that is impenetrable to x-rays located in the catheter lumen and is rotatably connected to an external controller such that it may be rotated about a central axis to block x-rays from reaching non-selected tissue as shown in FIGS. 4a and 4b. X-ray shield 15 may be connected to a rotatable knob located at the proximal end of apparatus 1 so that x-ray shield 15 may be manually or otherwise adjusted to the desired location, which is typically opposite the site of treatment.

Device 1 preferably includes separate lumen for receiving a miniaturized camera, that may be retractably inserted into the body lumen. The camera is connected to a viewing screen so that the physician can view the position of the device in the body lumen.

An important advantage of a device embodied above compared to apparatus of the prior art is easily discerned by comparing the device of FIG. 3 with the prior art apparatus of FIG. 1. As shown in FIG. 2, the x-ray pattern of the prior art device extends circumferentially from the location of the x-ray source in an unidirectional manner so that selected and non-selected tissue is irradiated. The x-ray shield of the subject apparatus limits allows medical personnel to limit radiation exposure to substantially only selected tissue, reducing exposure of healthy tissue to x-rays.

Figure 5:
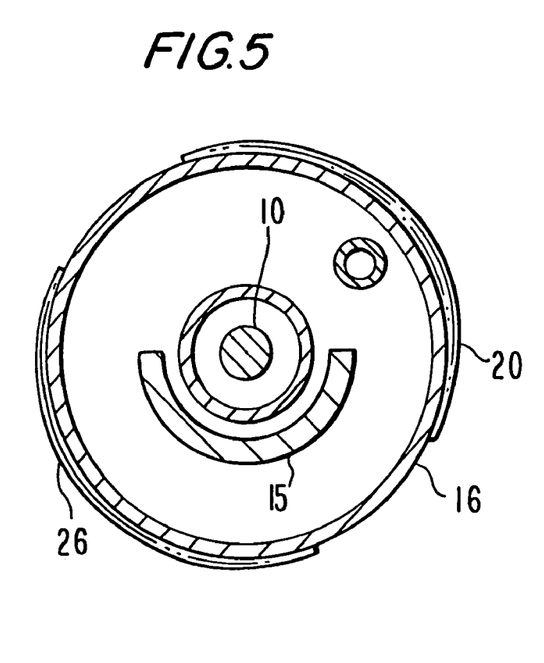
FIG. 5 is a cross-section of a catheter having circulation lumens to inflate positioning and/or anchoring balloons.
Figure 6:
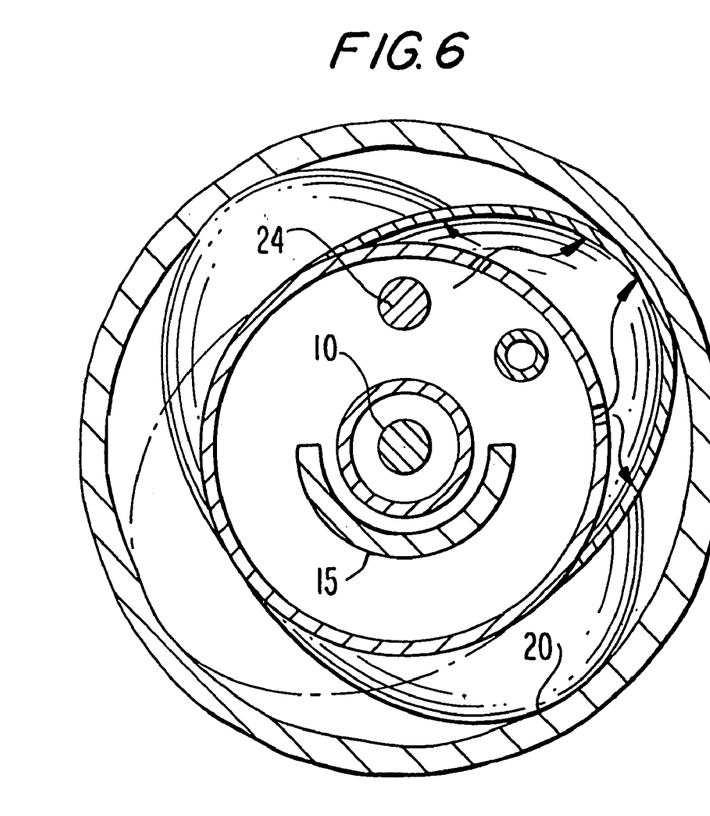
FIG. 6 is the catheter of FIG. 5 showing inflated positioning and/or anchoring balloons.
Figure 7:
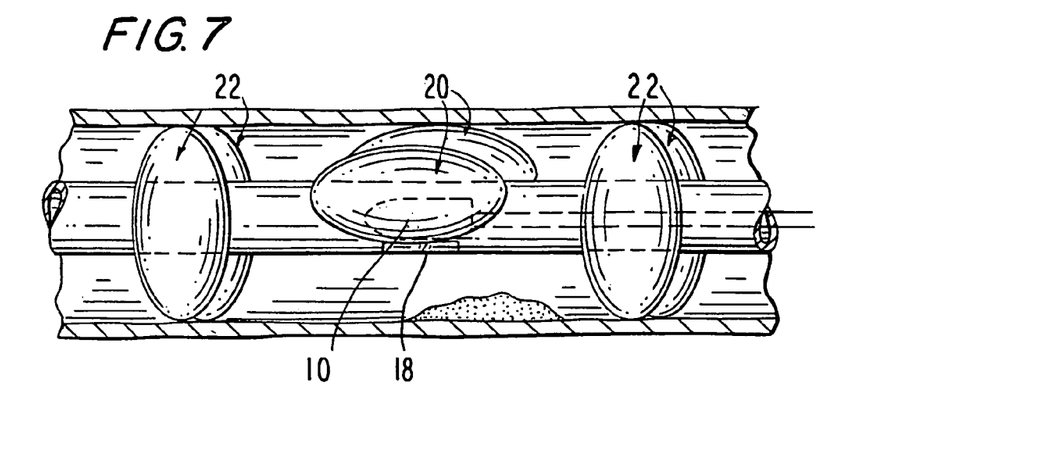
FIG. 7 is a miniature x-ray device having both positioning and anchoring balloons.
Figure 8:
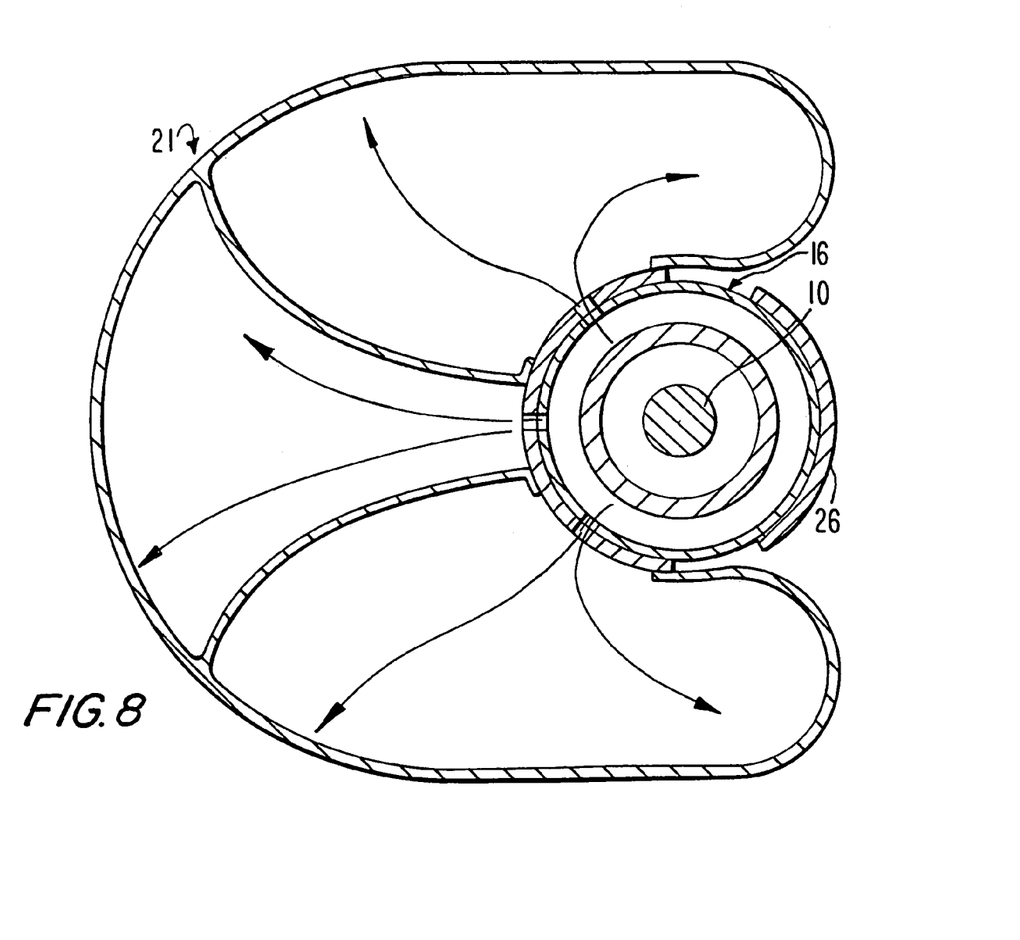
FIG. 8 is an embodiment of a miniature x-ray device having a multi-chambered balloon filled with coolant and having a thermocouple.

A preferred embodiment, shown in FIGS. 5, 6 and 7 includes at least one inflatable positioning balloon 20 adhered to the outer wall of the x-ray tube. Positioning balloon 20 communicates with a gas or liquid reservoir via a duct and is inflated after proper positioning of the apparatus in the body lumen so that the position of the x-ray source is maintained throughout treatment. Positioning balloon 20 may be adhered to the exterior wall of the x-ray tube by a suitable adhesive. Alternatively, the balloons are positioned in compartments located inside a lumen of the device or in recesses provided in x-ray tube 16 so that they are not exposed until needed. It is preferred that a plurality of balloons are provided. Alternatively, a multi-chambered balloon 21 is provided to aid proper positioning of the apparatus in the body lumen as shown in FIG. 8.

In a particularly preferred embodiment, a gas or liquid coolant is passed through balloon 20 via circulation lumens which communicate with the interior of positioning balloon 20 and are connected to a gas or liquid reservoir. A respective circulation duct is provided for each balloon or balloon chamber so that they may be independently inflated. The positioning balloons 20 may be inflated with a gas or a liquid, but an x-ray absorbent liquid is preferred. Normal saline is a particularly preferred liquid because it has a high heat capacity, is x-ray absorbent, and, in the unlikely event of leakage, is biocompatible with the patient.

Optionally, anchoring balloons 22 may be positioned proximal and distal to positioning balloon 20 to steadfastly anchor the apparatus in the desired site by fully inflating the anchor balloons, and finer positioning adjustments may be made with positioning balloons 20 which are placed nearly adjacent the x-ray source. In a particularly preferred embodiment, anchoring balloons 20 are positioned proximal and distal to the x-ray window to anchor the endoscopic device at the desired site.

Thermocouple 26 may be optionally affixed or placed in the vicinity of the x-ray source to measure temperature during the procedure. Thermocouple 26 may be in the form of a bimetallic strip and is operatively connected to a temperature display device so that the temperature is monitored during the procedure.

Apparatus preferably includes a camera catheter 24 to view inside the body cavity so that the endoscope can be properly positioned at the desired site. The guide may be positioned in the same tube as the x-ray source or may be positioned in a tube parallel to the x-ray source 7.

Figure 9:
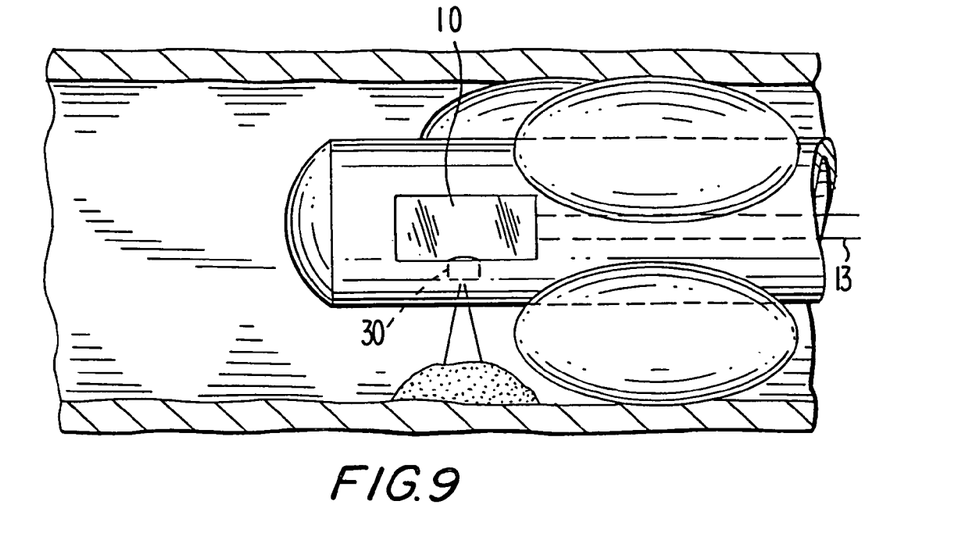
FIG. 9 is a preferred embodiment of a miniature x-ray device having a laser positioning system according to the invention.
Figure 10:
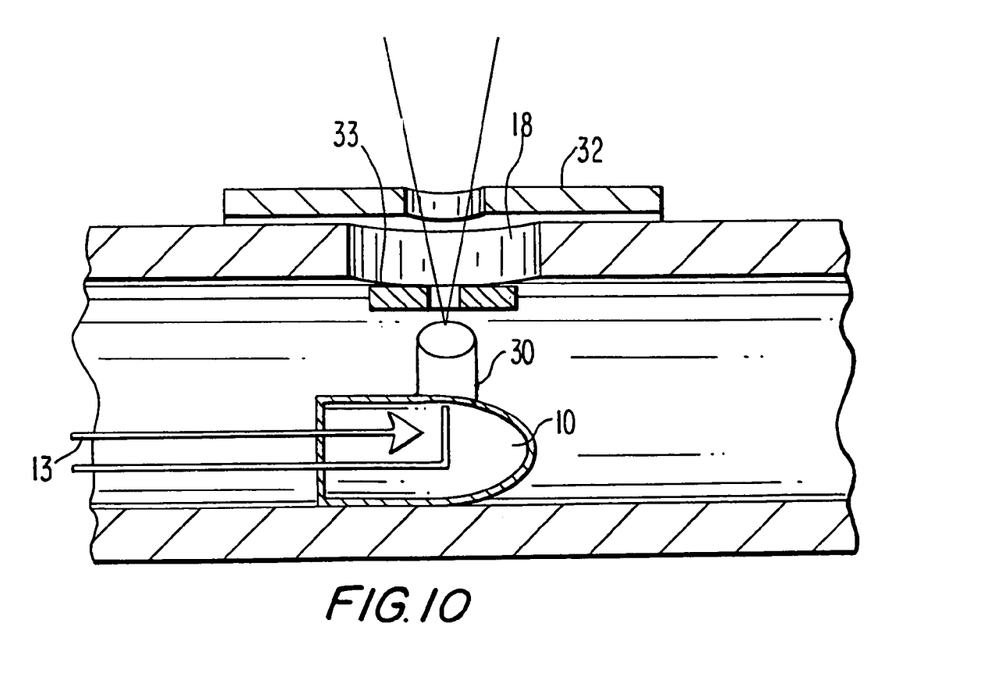
FIG. 10 is a cross section of a miniature x-ray device having a laser positioning system showing operation of the laser and x-ray shutters.

In a particularly preferred embodiment shown in FIGS. 9 and 10 a light source 30 is provided in the x-ray catheter and is used to position the device such that substantially only the desired site is irradiated. Light source 30 is preferably a laser, but other types of illuminating devices may also be used. Light source 30 is positioned inside the catheter lumen in the vicinity of x-ray source 10, but is a sufficient distance from the source so that the light source is not damaged during operation. Alternatively, light source 30 may be separated from x-ray source 10 by a suitable insulating material. Light source 30 is operatively connected to a power source.

Laser shutter 32 and x-ray shutter 33 are positioned one above the other and are independently opened and closed via an operable connection with respective manual opening devices. In a preferred embodiment, x-ray shutter 33 is automatically opened by an opening means when the x-ray is activated so that it is only open during periods of operation of the x-ray source, and closes when the x-ray source is not activated. The shutters operate in a known manner and are formed by a plurality of retractable portions (32a and 32b; and 33a and 33b) which operate in conjunction with their respective counterpart to form an aperture through which light and x-ray may pass.

In operation, the selected site is illuminated as shown in FIG. 9 with light source 33, and the field of illumination substantially corresponds with the field of irradiation. Thus, by simply illuminating the site of operation and viewing with the camera, it is possible to determine the site of radiation prior to irradiation with the x-ray. Then the anchor and positioning balloons can be properly adjusted, and the site can be irradiated with the dose of x-ray.

Figure 11:
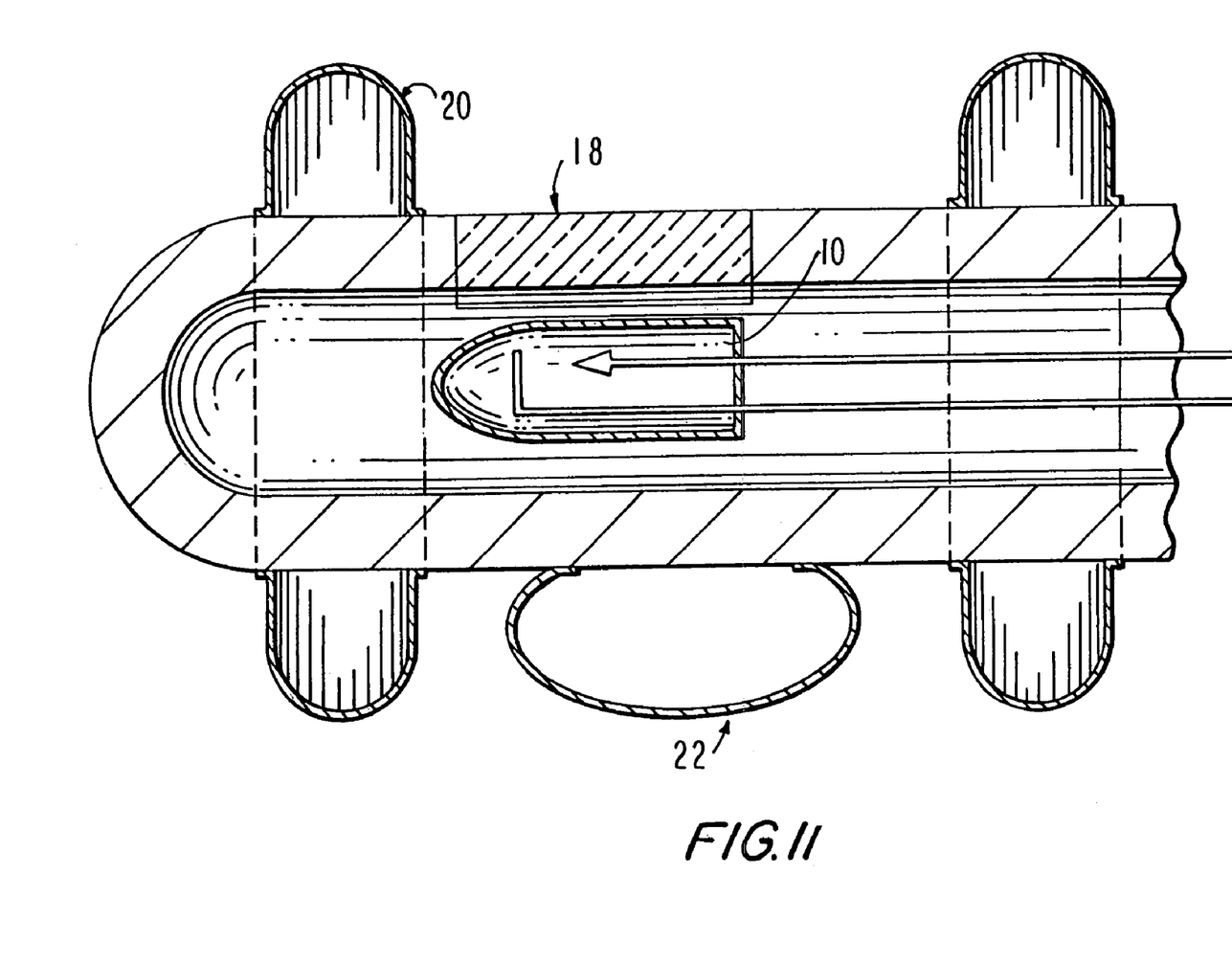
FIG. 11 is a preferred embodiment of a miniature x-ray catheter x-ray having an x-ray source located inside a catheter having an x-ray transparent window and a balloon positioning system.

FIG. 11 is an embodiment of a miniaturized x-ray device 100 having an x-ray source 101 attached to electrically conductive cable 102 which has an inflatable balloons 20 adhered to an outer surface thereof. The balloons communicate with a fluid or gas source as described above to aid positioning of the x-ray source at the desired site.

The present invention also relates to methods of treatment, prophylaxis and adjunctive therapy using the miniaturized x-ray apparatus of the present invention. Suitable for use with other endoscopic equipment, the x-ray device is of an appropriate size such that it may be used to treat cancers of bodily lumens such as colorectal cancer, vaginal cancer, esophageal cancer, pulmonary cancers such as lung cancers, stomach cancer, oral cancers, or any cancer accessible by a bodily lumen by positioning the device adjacent the target tissue and irradiating the tissue with a therapeutically effective amount of x-rays. In similar fashion, one can treat pre-cancerous conditions or conditions related with cancer such as gastroesophageal reflux disease (GERD). Preferably, the selected site is illuminated prior to irradiation such that field of irradiated tissue is determined prior to irradiation of the site.

The apparatus of the invention may be used in conjunction with imaging devices such as visual, x-ray, magnetic or ultrasound to aid in positioning of the device inside a body lumen.

Although the present invention has been shown and described with respect to several preferred embodiments thereof, additional embodiments will be apparent to the skilled artisan without departing from the spirit and scope of the invention.

All cited references are incorporated herein by reference.

What is claimed is:

1. An apparatus comprising:
   an x-ray catheter comprising an x-ray tube having an x-ray source therein, wherein said x-ray source is connected to an electric power supply;
   an x-ray shield that is impenetrable to x-rays positioned in said x-ray tube; and
   wherein said x-ray shield is rotatable.

2. The apparatus of claim 1, further comprising an x-ray transparent window at a distal end of said x-ray tube.

3. The apparatus of claim 1, further comprising inflatable anchoring or positioning balloons affixed to an outer wall of the catheter and operably connected to a gas or liquid reservoir by transport ducts.

4. The apparatus of claim 1, further comprising a thermocouple for measuring temperature.

5. The apparatus of claim 1, further comprising a light source and an x-ray shutter for controlling the flow of x-rays and light through said x-ray transparent window, said window also being transparent to light.

6. The apparatus of claim 1, wherein said x-ray shield is connected to an external controller.

7. The apparatus of claim 6, wherein said external controller is a rotatable knob located at a proximal end of the apparatus.

8. The apparatus of claim 2, wherein said x-ray transparent window comprises at least one material selected from the group consisting of glass beryllium, ceramic, plastic and mica.

9. The apparatus of claim 1, further comprising inflatable anchoring or positioning balloons affixed to an outer wall of the apparatus.

10. A method comprising:
    positioning an x-ray source of an apparatus adjacent a selected cancerous site having a cancerous condition in a body lumen and irradiating the cancerous site with a therapeutically effective dose of x-ray radiation to treat the cancerous condition, wherein said apparatus comprises an x-ray catheter comprising an x-ray tube having an x-ray source therein, wherein said x-ray source is connected to an electric power supply; and
    an x-ray shield that is impenetrable to x-rays positioned in said x-ray tube, wherein said x-ray shield is rotatable.

11. The method of claim 10, wherein the cancer is selected from the group consisting of colorectal cancer, vaginal cancer, pulmonary cancer, esophageal cancer, oral cancer, and stomach cancer.

12. The method of claim 10, wherein the cancer is colorectal cancer.

13. An apparatus for delivery x-rays to a selected site within a body cavity comprising:
    a catheter having at least one lumen and an x-ray transparent window at a distal end thereof;
    an x-ray source in said at least one lumen adjacent said x-ray transparent window,
    a x-ray shield positioned to direct x-rays from said source through said x-ray transparent window to said selected site; said x-ray shield being operably connected to an external controller to rotate said x-ray shield when said catheter is inserted in a body cavity;
    wherein said x-ray shield is rotatable about a central axis.

14. The apparatus of claim 13, further comprising inflatable anchoring or positioning balloons affixed to an outer wall of the catheter and operably connected to a gas or liquid reservoir by transport ducts.

15. The apparatus of claim 13, further comprising a thermocouple for measuring temperature.

16. The apparatus of claim 13, further comprising a light source and an x-ray shutter for controlling the flow of x-rays and light through said x-ray transparent window, said window also being transparent to light.

17. The apparatus of claim 13, wherein said x-ray shield is connected to an external controller.

18. The apparatus of claim 17, wherein said external controller is a rotatable knob located at a proximal end of the apparatus.

19. The apparatus of claim 13, wherein said x-ray transparent window comprises at least one material selected from the group consisting of glass beryllium, ceramic, plastic and mica.

20. The apparatus of claim 13, further comprising inflatable anchoring or positioning balloons affixed to an outer wall of the apparatus.

21. A method comprising:

positioning an x-ray source of an apparatus adjacent a selected cancerous site in a body lumen and irradiating the cancerous site with, therapeutically effective dose of x-ray radiation to treat the cancer, wherein said apparatus comprises a catheter having at least one lumen, and an x-ray transparent window at a distal end thereof;

an x-ray source in said at least one lumen adjacent said x-ray transparent window, a x-ray shield positioned to direct x-rays from said source through said x-ray transparent window to said selected site; said x-ray shield being operably connected to an external controller to rotate said x-ray shield when said catheter is inserted in a body cavity;

wherein said x-ray shield is rotatable about a central axis.

22. The method of claim 21, wherein the cancer is selected from the group consisting of colorectal cancer, vaginal cancer, pulmonary cancer, esophageal cancer, oral cancer, and stomach cancer.

23. The method of claim 22, wherein the cancer is colorectal cancer.

24. A method comprising: positioning an x-ray source of an apparatus adjacent a selected precancerous site having a precancerous condition in a body lumen and irradiating the precancerous site with a therapeutically effective dose of x-ray radiation to treat the precancerous condition, wherein said apparatus comprises a catheter having at least one lumen and an x-ray transparent window at a distal end thereof an x-ray source in said at least one lumen adjacent said x-ray transparent window, a x-ray shield positioned to direct x-rays from said source through said x-ray transparent window to said selected site; said x-ray shield being operably connected to an external controller to rotate said x-ray shield when said catheter is inserted in a body cavity;

wherein said x-ray shield is rotatable about a central axis.

25. A method comprising:

positioning an x-ray source of an apparatus adjacent a selected precancerous site in a body lumen and irradiating the precancerous site with a therapeutically effective dose of x-ray radiation, wherein said apparatus comprises an x-ray catheter comprising an x-ray tube having an x-ray source therein, wherein said x-ray source is connected to an electric power supply; and an x-ray shield that is impenetrable to x-rays positioned in said x-ray tube, wherein said x-ray shield is rotatable.

26. A method comprising:

positioning an x-ray source of an apparatus adjacent a selected precancerous site in a body lumen and irradiating the precancerous site with a therapeutically effective dose of x-ray radiation; wherein said apparatus comprises a catheter having at least one lumen and an x-ray transparent window at a distal end thereof;

an x-ray source in said at least one lumen adjacent said x-ray transparent window, an x-ray shield positioned to direct x-rays from said source through said x-ray transparent window to said selected site; said x-ray shield being operably connected to an external controller to rotate said x-ray shield when said catheter is inserted in a body cavity;

wherein said x-ray shield is rotatable about a central axis.

27. A method comprising inserting the apparatus of claim 1 into a lumen of a patient, positioning the x-ray source next to a desired site in said lumen, and irradiating said desired site with x-rays from said x-ray source.

28. A method comprising inserting the apparatus of claim 13 into a lumen of a patient, positioning the x-ray source next to a desired site in said lumen, and irradiating said desired site with x-rays from said x-ray source.

* * * * *